United States Patent
Lee et al.

(10) Patent No.: US 7,018,814 B2
(45) Date of Patent: Mar. 28, 2006

(54) PROCESS OF PURIFYING VANCOMYCIN HYDROCHLORIDE

(75) Inventors: Ju Won Lee, Bucheon (KR); Yun Taek Jung, Seoul (KR); Jung Woo Suh, Seoul (KR); Kwang Seob Lee, Yongin (KR)

(73) Assignee: CJ Corporation, Seoul (KR)

( * ) Notice: Subject to any disclaimer, the term of this patent is extended or adjusted under 35 U.S.C. 154(b) by 0 days.

(21) Appl. No.: 10/943,404

(22) Filed: Sep. 17, 2004

(65) Prior Publication Data

US 2006/0003406 A1    Jan. 5, 2006

(30) Foreign Application Priority Data

Jun. 30, 2004    (KR) .................. 10-2004-0050429

(51) Int. Cl.
*C12P 21/04*     (2006.01)
*C12P 19/44*     (2006.01)
*A61K 38/12*     (2006.01)
*C07K 1/14*      (2006.01)
*C07K 9/00*      (2006.01)

(52) U.S. Cl. ................. 435/71.3; 424/124; 435/76; 530/344

(58) Field of Classification Search ............... 435/71.3, 435/76; 424/124; 530/344
See application file for complete search history.

(56) References Cited

U.S. PATENT DOCUMENTS

| 4,440,753 A |   | 4/1984  | McCormick et al. |
|---|---|---|---|
| 4,845,194 A |   | 7/1989  | Glass et al. |
| 5,037,652 A |   | 8/1991  | Catt et al. |
| 5,149,784 A |   | 9/1992  | Chu |
| 5,223,413 A | * | 6/1993  | Nagy et al. ................ 435/71.3 |
| 5,235,037 A |   | 8/1993  | Krishnan |
| 5,258,495 A |   | 11/1993 | Chu |
| 5,574,135 A |   | 11/1996 | Chu |
| 5,853,720 A | * | 12/1998 | Pflaum et al. .............. 424/124 |

* cited by examiner

*Primary Examiner*—Herbert J. Lilling
(74) *Attorney, Agent, or Firm*—Rothwell, Figg, Ernst & Manbeck, P.C.

(57) ABSTRACT

Provided is a method of purifying a vancomycin from a fermentation broth of a microorganism containing vancomycin, including passing the fermentation broth of a microorganism containing vancomycin through a strong acid cation exchange resin, a weak base anion exchange resin, alumina and a hydrophobic absorbent resin sequentially.

6 Claims, 1 Drawing Sheet

PROCESS OF PURIFYING VANCOMYCIN HYDROCHLORIDE

BACKGROUND OF THE INVENTION

This application claims priority from Korean Patent Application No. 2004-50429, filed on Jun. 30, 2004, in the Korean Intellectual Property Office, the disclosure of which is incorporated herein in its entirety by reference.

1. Field of the Invention

The present invention relates to a method of purifying highly pure vancomycin HCl from a fermentation broth of a microorganism.

2. Description of the Related Art

Vancomycin is one of the glycopeptide antibiotics and produced by microorganisms of the genus *Actinomycetes*, such as the strain *Amycolatopsis orientalis* (ATCC 19795). Vancomycin exhibits a strong inhibition effect on gram positive bacteria, such as Streptococci, Staphylococci, *Clostridium difficile*, and gram positive bacteria resistant to penicillin and cephalosporin antibiotics. Also, vancomycin is known to have high treatment effects on diseases derived from methicillin-resistant *Staphylococcus aureus* (MRSA) which is fatal to post-operation, elderly patients, and persons having weak immunity. Vancomycin HCl is generally consumed as solution orally or in capsule form, or it is injected.

According to *European Pharmacopeia*, vancomycin be at least 93% pure and have impurities composing not more than 4% of the solution.

Conventional methods of purifying vancomycin are described in U.S. Pat. Nos. 4,440,753, 4,845,194, 5,037,652, 5,149,784, 5,235,037, 5,258,495, 5,574,135 etc. In order to increase a yield of vancomycin, in these methods, the fermentation broth is adjusted to a pH of 11 and filtered, and then the pH of the obtained filtrate is adjusted to 8. Next, the filtrate is passed through an absorbent resin, and then the vancomycin is eluted from the absorbent resin. This operation is repeated two or three times. Subsequently, a basic salt of vancomycin is crystallized with a solvent, and the obtained crystals are acidified. The acidified product is recrystallized with acetone or alcohol to produce vancomycin HCl. The process is very complicated since vancomycin HCl crystals are obtained by adjusting its pH several times, and after obtaining crystals of the basic salt of vancomycin as intermediates, vancomycin HCl are recrystallized. In addition, vancomycin may be unstable at a high pH. Especially, due to a residual colorant, the obtained vancomycin may be reddish in color and it is difficult to obtain vancomycin having a purity of at least 93%. Thus, it is difficult to produce vancomycin which may satisfy a specification prescribed in European Antibiotic Drugs Standards.

The present inventors conducted vigorous research to overcome these problems and discovered a method of producing highly pure vancomycin HCl, which may directly recover vancomycin HCl without a process of obtaining an intermediate, i.e., a basic salt of vancomycin, which is performed due to an increased pH of the product containing vancomycin, thus resulting in a simplified process, and may provide a highly pure vancomycin and especially, eliminate most colorants contained in vancomycin.

SUMMARY OF THE INVENTION

The present invention provides a method of purifying a highly pure vancomycin HCl from a fermentation broth of a microorganism containing vancomycin in a simplified process.

According to another aspect of the present invention, there is provided a method of purifying vancomycin HCl from a fermentation broth of a microorganism containing vancomycin, comprising: passing the fermentation broth of a microorganism containing vancomycin through a strong acid cation exchange resin at pH 1–3 and eluting vancomycin with a 0.05 to 0.2 N ammonium hydroxide solution in water having a pH of 9–11; adjusting a pH of the eluted solution to 3–5, passing the solution through a weak base anion exchange resin and subsequently alumina, and then washing the weak base anion exchange resin and alumina with water to elute vancomycin, and decolorizing vancomycin; passing the eluted solution through a hydrophobic absorbent resin and eluting vancomycin with an aqueous solution of C1–4 alcohol; and adding hydrochloric acid to the eluted solution to adjust the pH of the eluted solution to 2–5 and adding an water-soluble organic solvent selected from the group consisting of a C1–4 alcohol, acetonitrile, acetone, and methyl isobutyl ketone to the eluted solution to crystallize vancomycin HCl.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
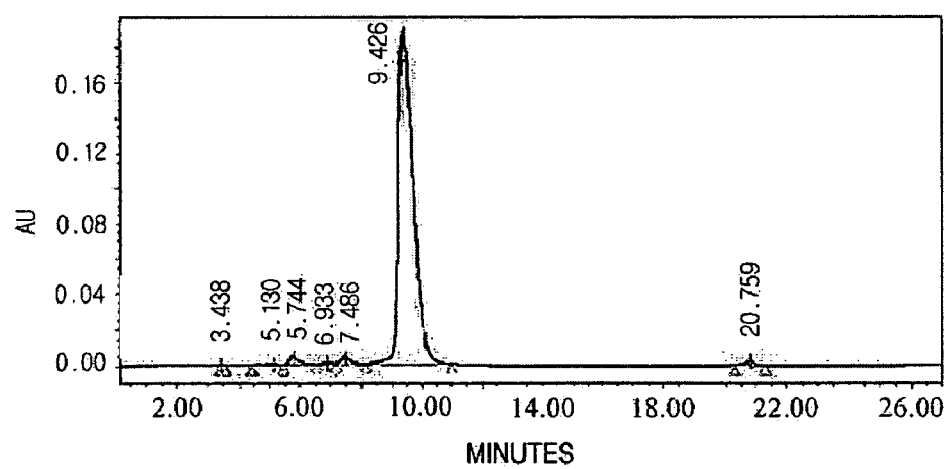
FIG. 1 is a view illustrating an HPLC analytical result of vancomycin HCl purified using a method according to an embodiment of the present invention.

According to an embodiment of the present invention, there is provided a method of purifying vancomycin HCl from a fermentation broth of a microorganism containing vancomycin, comprising: passing the fermentation broth of a microorganism containing vancomycin through a strong acid cation exchange resin with a pH of 1–3 and eluting vancomycin with a 0.05 to 0.2 N ammonium hydroxide solution in water having a pH of 9–11; adjusting a pH of the eluted solution to 3–5, passing the solution through a weak base anion exchange resin and subsequently alumina, and then washing the weak base anion exchange resin and alumina with water to elute vancomycin, and decolorizing vancomycin; passing the eluted solution through a hydrophobic absorbent resin and eluting vancomycin with an aqueous solution of C1–4 alcohol; and adding hydrochloric acid to the eluted solution to adjust the pH of the eluted solution to 2–5 and adding an water-soluble organic solvent selected from the group consisting of a C1–4 alcohol, acetonitrile, acetone, and methyl isobutyl ketone, preferably acetone, to the eluted solution to crystallize vancomycin HCl.

In the present embodiment, the fermentation broth of a microorganism containing vancomycin is passed through a strong acid cation exchange resin at pH 1–3 and an aqueous solution of ammonium hydroxide is eluted through the strong acid cation exchange resin. The microorganism may be any microorganism that produces vancomycin and accumulates the produced vancomycin in a culture. For example, a shaking culture of *Amycolatopsis orientalis*, more specifically *Amycolatopsis orientalis* (ATT 19795) may be used. The pH of the culture may be adjusted to 1–3 using an acid, such as a strong inorganic acid, such as hydrochloric acid and sulfuric acid. After the culture is left for a predetermined time, for example, 30 minutes, the microorganism and solid impurities are filtered off using a filtration funnel and the filtrate can be purified in the following process. The strong acid cation exchange resin is a compound which can adsorb a cation material in a strong acidic condition, preferably at a pH of 1–3. DOWEX 50WX2-100 (50–100 mesh, a sulfone resin, available from Dow chemical) may be used as a strong acid cation exchange resin. An ordinary person in the art will arbitrarily control a flow rate at which the fermentation is loaded on the cation exchange resin. For example, the flow rate may be 0.5 to 2.0 volumes of column. Elution may be performed with a solution of ammonium hydroxide, for example, a 0.05 to 0.2 N ammonium hydroxide solution in water having a pH of 9–11. The obtained vancomycin has a purity of at least 85%. As soon as the vancomycin solution is eluted, the pH of the vancomycin solution must be adjusted to 3–5 using an acid, for example, hydrochloric acid.

Then the resultant solution is passed through a weak base anion exchange resin and subsequently alumina, and then the weak base anion exchange resin and alumina were washed with water to elute vancomycin and decolorizing of the eluted vancomycin by adsoption. For example, DC11 (a porous acrylic resin, available from MITSUBISHI) may be used as the weak base anion exchange resin and an activated alumina may be used as the alumina (~150 mesh, acidic activated, available from ALDRICH).

In an exemplary embodiment of the present invention, the eluted solution obtained after the decolorizing may be further mixed with activated carbon and then stirred, followed by filtration to further decolorize the vancomycin. The amount of activated carbon used may be, for example, 10% based on the amount of vancomycin. The purity of the decolorized vancomycin in water increases to about 90%.

The eluted solution obtained after the decolorizing may be passed through a hydrophobic absorbent resin and eluting is performed with an aqueous solution of C1–4 alcohol. Conventional hydrophobic resin used in reverse phase chromatography may be used as the hydrophobic absorbent resin for example, AMBERCHROM CG-161M (particle size: 75 μm, available from ROHM & HAAS). The C1–4 alcohol solution may be a solution of alcohol selected from the group consisting of methanol, ethanol, and isopropanol. The C1–4 alcohol solution may further contain inorganic salts, such as anhydrous sodium phosphate ($NaH_2PO_4$), for example, in a concentration of 50 mM. Gradient elution can be applied to increase the elution efficiency of vancomycin. An ordinary person in the art can easily determine a process of performing the gradient elution through a suitable preliminary experiment. The vancomycin obtained by eluting with the C1–4 alcohol has a purity of at least 95% as determined by an HPLC analysis based on *European Pharmcopeia*.

In another exemplary embodiment of the present invention, the eluted solution obtained by eluting the vancomycin with an aqueous solution of C1–4 alcohol may be further concentrated. The eluted solution may be concentrated using conventional methods known in the art, such as reverse osmosis and vacuum drying, etc.

Hydrochloric acid may be added to the eluted solution obtained by eluting the vancomycin with an aqueous solution of C1–4 alcohol to adjust the pH of the eluted solution to 2–5 and then, an water-soluble organic solvent selected from the group consisting of a C1–4 alcohol, acetonitrile, acetone, and methyl isobutyl ketone, preferably acetone, may be added to the eluted solution to crystallize vancomycin HCl. For example, the eluted solution is concentrated using reverse osmosis and hydrochloric acid is added thereto to adjust the pH of the eluted solution to 2–5, and then acetone is added to the eluted solution in an amount of 5 fold by volume of the eluted solution. The solution is then left at a temperature of about 2 to 8° C. for a predetermined time, for example, about 20 hours, to obtain vancomycin crystals. The obtained vancomycin crystals are filtered off and then dried in a vacuum dryer to recover vancomycin HCl. The resultant vancomycin HCl has a purity of at least 95% as determined by the HPLC analysis based on *European Pharmcopeia* and has an antimicrobial threshold of at least 1,000 mcg/ml. Thus, according to the method in an embodiment of the present invention, highly pure vancomycin can be obtained in a simplified purification process.

Hereinafter, the present invention will be described in more detail with reference to the following examples. However, these examples are given for the purpose of illustration and are not intended to limit the scope of the invention.

EXAMPLE

Example 1

Purification Using a Strong Acid Cation Exchange Resin (DOWEX 50WX2100)

Sulfuric acid was added to 6,000 ml of a fermentation broth of *Amycolatopsis orientalis* (ATCC 19795) containing vancomycin in a concentration of 5,000 mg/L to adjust the pH to 2. The adjusted culture was left for 30 min, and then filtered through a filter of diatomaceous earth to obtain 7,500 ml of a filtrate.

The concentrated filtrate was passed through 2,000 ml of a strong acid cation exchange resin DOWEX 50WX2-100 (DOW CHEMICAL) at a flow rate of 2,000 ml/hr and adsorbed thereto. Next, the resin was washed with 4,000 ml distilled water at a flow rate of 2,000 ml/hr. After washing, the vancomycin was eluted from DOWEX 50WX2-100 using 5,000 ml of a 0.1 N $NH_4OH$ aqueous solution to obtain 4,500 ml of the eluted solution (yield: 88%). As soon as the eluted solution was obtained, 2 N HCl was added to the eluted solution to adjust the pH to 3.5.

Example 2

Purification Using a Weak Base Anion Exchange Resin and Alumina 4,500 ml of the eluted solution obtained in Example 1 was passed through 1,000 ml of a weak base anion exchange resin DCA11 (MITSUBISHI, Japan) and subsequently 800 ml of activated carbon (ALDRICH, U.S.A.) at a flow rate of 1,000 ml/hr. Then, DCA11 and alumina were washed with 2,000 ml of water at a flow rate of 1,000 ml/hr.

Next, 15 g of activated carbon was placed into the obtained eluted solution, stirred for 20 minutes and then filtered off. The volume of the eluted solution was 4,800 ml (yield: 85%).

Example 3

Purification Using a Hydrophobic Absorbent Resin (AMBERCHROM CG-161M)

4,800 ml of the eluted solution obtained in Example 2 was passed through 500 ml of a hydrophobic absorbent resin AMBERCHROM CG-161M (ROHM & HAAS) at a flow rate of 1,000 ml/hr and adsorbed thereto. Then, the resin was washed with 1,000 ml of water at a flow rate of 1,000 ml/hr. After washing, the vancomycin was eluted at a flow rate of 1,000 ml/hr using an increasing concentration of isopropanol containing 50 mM anhydrous sodium phosphate ($NaH_2PO_4$) in the water eluant, to 8% for 2.5 hours at a constant rate. At this time, fractions of 400 ml were obtained and subjected to HPLC analysis based on European Antibiotic Drugs Standards to determine the purity of the vancomycin. Then, the fractions with a purity of at least 93% were combined to recover the vancomycin. The combined fractions had a volume of 1,400 ml and contained at least 95% of vancomycin with most colorants removed therefrom.

Example 4

Recovery and Analysis of the Vancomycin Crystals

The eluted solution obtained in Example 3 was concentrated using reverse osmosis (R/O) to a volume of 400 ml. The same volume of water was added to the concentrated solution and then, the solution was again concentrated using reverse osmosis (R/O) to a volume of 400 ml. The similar procedure was repeated 12 times to concentrate the solution to a volume of 100 ml. The concentrated solution was adjusted to a pH of 3.2 using 2 N HCl. Then, acetone was added dropwise slowly to the solution, a volume of acetone added being a 5 fold volume of the solution. The solution was left at 4° C. overnight, and then filtered off. The filtered precipitate was dried in a vacuum dryer at 40° C. or below. The dried vancomycin HCl had a weight of 13,500 mg and determined by HPLC analysis based on *European Pharmcopeia,* 2001. In addition, a commercial vancomycin HCl (LILLY, Japan) was used as a control.

Figure 2:
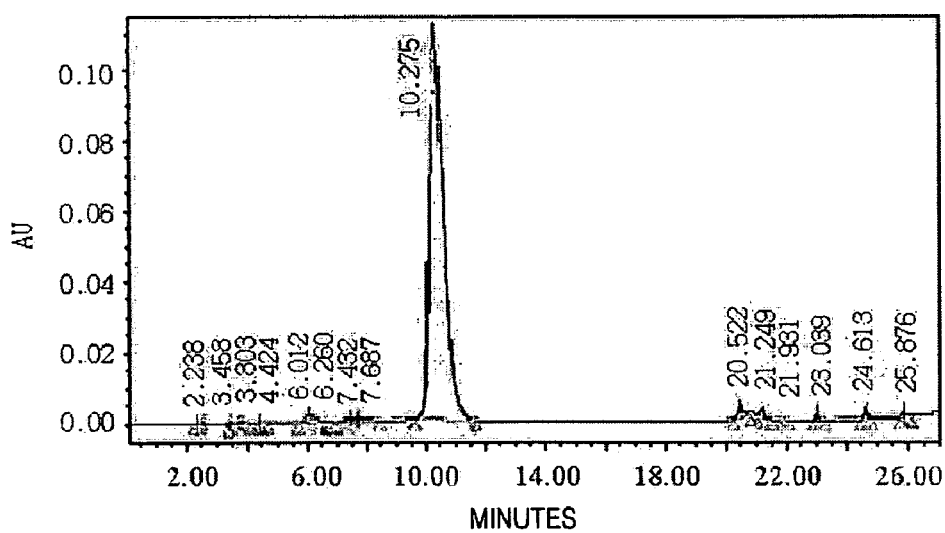
FIG. 2 is a view illustrating an HPLC analytical result (based on European Antibiotic Drugs Standards) of vancomycin HCl available from LILLY, Japan.

The results are illustrated in FIGS. 1 and 2. As illustrated in FIG. 1, using a method according to an embodiment of the present invention, highly pure vancomycin HCl was obtained, which had a vancomycin content of 95.5% and an antimicrobial activity of at least 1,024 mcg/mg. Meanwhile, as illustrated in FIG. 2, the commercial vancomycin HCl had a vancomycin content of about 93% and had many colorants therein compared to the vancomycin purfied according to the present invention.

Thus, vancomycin HCl obtained using the purification method according to an embodiment of the present invention had a purity of at least 95% and had a remarkably decreased content of colorants.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of purifying vancomycin HCl from a fermentation broth of a microorganism containing vancomycin, comprising:
   passing the fermentation broth of a microorganism containing vancomycin through a strong acid cation exchange resin at pH 1–3 and eluting vancomycin with a 0.05 to 0.2 N ammonium hydroxide solution in water having a pH of 9–11;
   adjusting a pH of the eluted solution to 3–5, passing the solution through a weak base anion exchange resin and subsequently alumina, and then washing the weak base anion exchange resin and alumina with water to elute vancomycin, and decolorizing vancomycin;
   passing the eluted solution through a hydrophobic absorbent resin and eluting vancomycin with an aqueous solution of C1–4 alcohol; and
   adding hydrochloric acid to the eluted solution to adjust the pH of the eluted solution to 2–5 and adding an water-soluble organic solvent selected from the group consisting of a C1–4 alcohol, acetonitrile, acetone, and methyl isobutyl ketone to the eluted solution to crystallize vancomycin HCl.

2. The method of claim 1, wherein the microorganism is *Amycolatopisis orientalis*.

3. The method of claim 1, wherein the strong acid cation exchange resin is, a sulfone resin, available which has 50–100 mesh.

4. The method of claim 1, wherein in the eluting vancomycin with an aqueous solution of C1–4 alcohol and in the adding the water-soluble organic solvent to the eluted solution, a C1–4 alcohol is selected from the group consisting of methanol, ethanol, and isopropanol.

5. The method of claim 1, further comprising mixing the eluted solution obtained after the decolorizing with activated carbon, and then filtering the resultant mixture.

6. The method of claim 1, further comprising concentrating the eluted solution obtained after the eluting vancomycin with the aqueous solution of C1–4 alcohol.

* * * * *